| United States Patent [19] | [11] | 4,377,713 |
|---|---|---|
| Keblys | [45] | *Mar. 22, 1983 |

[54] CHEMICAL PROCESS FOR PREPARING 3-PHENOXYBENZYL CHLORIDE

[75] Inventor: Kestutis A. Keblys, Southfield, Mich.

[73] Assignee: Ethyl Corporation, Richmond, Va.

[*] Notice: The portion of the term of this patent subsequent to Apr. 20, 1999, has been disclaimed.

[21] Appl. No.: 340,321

[22] Filed: Jan. 18, 1982

Related U.S. Application Data

[63] Continuation-in-part of Ser. No. 836,428, Sep. 26, 1977, Pat. No. 4,326,089.

[51] Int. Cl.$^3$ ............................................. C07C 41/22
[52] U.S. Cl. .................................................. 568/639
[58] Field of Search ......................................... 568/639

[56] References Cited

U.S. PATENT DOCUMENTS

| 2,816,144 | 12/1957 | Harris | 260/599 |
|---|---|---|---|
| 3,996,291 | 12/1976 | Dietrich et al. | 568/437 |
| 4,010,087 | 3/1977 | Wood et al. | 204/158 |
| 4,014,940 | 3/1977 | Ume et al. | 260/612 |
| 4,108,904 | 8/1978 | Brown et al. | 568/639 X |
| 4,146,737 | 3/1979 | Sheldon et al. | 568/639 |
| 4,326,089 | 4/1982 | Keblys | 568/639 |

OTHER PUBLICATIONS

Engelsma et al., Rec. Trav. Chim. Pays–Bas, vol. 80, (1961), 526–532.

*Primary Examiner*—Bernard Helfin
*Attorney, Agent, or Firm*—Donald L. Johnson; Joseph D. Odenweller; John F. Hunt

[57] ABSTRACT

Reaction of 3-phenoxytoluene with bromine at elevated temperature yields 3-phenoxybenzyl bromide, 3-phenoxybenzal bromide, or a mixture thereof. In contrast to teachings of the prior art, phosphorus halide catalysis or u.v. activation is not required to achieve a desirable amount of side-chain bromination with a minimum of nuclear halogenation. For example, it was observed that at 265±5° C., good yields of the desired benzyl and benzal bromide were obtained, but no nuclear halogenated by-product was detected by gas chromatography. The comparable chlorination is also effective.

3 Claims, No Drawings

CHEMICAL PROCESS FOR PREPARING 3-PHENOXYBENZYL CHLORIDE

CROSS REFERENCE TO RELATED APPLICATION

This application is a continuation-in-part of Ser. No. 836,428, filed Sept. 26, 1977 now U.S. Pat. No. 4,326,089.

BACKGROUND OF THE INVENTION

The invention pertains to preparation of m-phenoxybenzyl and m-phenoxybenzal halides. These products are useful as pesticide intermediates. In particular this invention relates to a process for reacting m-phenoxytoluene and a halogen at a temperature high enough to give, (i) a good yield of one or both of the aforementioned compounds, and (ii) an acceptable low amount of undesirable nuclear brominated by-product. The process is characterized further by being conducted without added phosphorus halide catalysis and without activation with ultra-violet radiation.

Thus, the process of this invention differs from the closest known prior art, viz U.S. Pat. No. 4,014,940, U.S. 4,010,087. More particularly, U.S. Pat. No. 4,014,940, teaches the use of phosphorus halide catalysis and that appreciable aromatic halogenation can occur if such catalysis is not used. The other patent, U.S. Pat. No. 4,010,087, teaches u.v. irradiation of the reaction mixture.

In Examples I–IV of the patent which illustrate batch reactions, the yield of ring brominated by-product was 2–30%. With u.v. light and a continuous reaction, (Example V) almost no ring brominated material could be detected in the product.

SUMMARY OF THE INVENTION

In a main aspect, this invention comprises the discovery that thermal bromination of m-phenoxytoluene proceeds satisfactorily. Thus, this invention comprises the discovery that good quality product can be obtained without resorting to catalysis and activation expedients taught by the prior art. The process of this invention therefore holds promise for commercial application. Phosphorus halide catalysis expense and disposal of spent or waste phosphorus values are not associated with the process of invention, while these are inherent drawbacks in the process of U.S. Pat. No. 4,014,940. Similarly, the process of this invention does not suffer from the problems associated with u.v. radiation used in commercial scale production.

The process of this invention, which comprises a thermal bromination, without added catalyst or activating irradiation, is illustrated by the following preferred embodiments:

A process for preparing m-phenoxybenzyl halide, or m-phenoxybenzal halide, or a mixture thereof, said process comprising halogenating m-phenoxytoluene with a halogen at a temperature above about 220° C., said process being conducted in the substantial absence of a phosphorus halide and in the substantial absence of increased u.v. radiation.

A process for preparing a product selected from the class consisting of m-phenoxybenzyl bromide, m-phenoxybenzal bromide, and mixtures thereof, said process comprising reacting about 0.7–2.5 moles of bromine with each one mole quantity of m-phenoxytoluene at a temperature of about 260°–270° C., said process being carried out in the substantial absence of added u.v. radiation and in the substantial absence of phosphorus halide.

A process for preparing m-phenoxybenzyl chloride, or m-phenoxybenzal chloride, or a mixture thereof, said process comprising chlorinating m-phenoxytoluene with chlorine at a temperature above about =50° C., said process being conducted in the absence of a catalyst and in the absence of added u.v. radiation, said process being characterized by formation of a low amount of nuclear chlorinated by-product.

A process for preparing a product selected from the class consisting of m-phenoxybenzyl chloride, m-phenoxybenzal chloride, and mixtures thereof, said process comprising reacting about 0.7–2.5 moles of chlorine with each one mole quantity of m-phenoxytoluene at a temperature of about 260°–270° C., said process being carried out in the absence of added u.v. radiation and in the absence of phosphorous halide, said process being characterized by formation of a low amount of nuclear chlorinated by-product.

The side chain-halogenated products
m-phenoxybenzyl chloride,
m-phenoxybenzal chloride,
m-phenoxybenzyl bromide, and
m-phenoxybenzal bromide
are used for preparing pyrethroid insecticides. These materials are highly active against insects but have low mammalian toxicity.

DESCRIPTION OF PREFERRED EMBODIMENTS

The process of this invention comprises mixing a bromine source with m-phenoxytoluene under suitable reaction conditions. As well known, reaction of m-phenoxytoluene with bromine to prepare 3-phenoxybenzyl bromide entails interaction of equimolar amounts of the reactants, while preparation of the benzal bromide entails substitution of two moles of bromine per mole of the m-phenoxytoluene. However, the reactant ratio used in this process is not critical, and an excess of either reactant can be used. Thus, it has been found that good results are obtained when slightly more than equimolar portions of bromine are used. Hence, one may use about 1.01 to about 1.3 moles of bromine per mole of m-phenoxytoluene. As illustrated by the examples below, an excess of bromine can afford 3-phenoxybenzyl bromide as the major product admixed with some 3-phenoxybenzal bromide. Also illustrated are comparable productions of 3-phenoxybenzal chloride and 3-phenoxybenzyl chloride.

The reaction can be conducted in the presence or absence of an essentially inert, organic solvent. Preferably no solvent is employed. An excess of the m-phenoxytoluene can be used as a diluent, if desired.

Good results are obtained by adding the bromine or chlorine to the other reactant. The rate of bromine introduction is slow enough to avoid or lessen build up a high local concentration of bromine which may favor further, undesired bromination.

The reaction time is at least somewhat dependent on the other reaction conditions employed, such as temperature. In many instances reaction times over one hour are efficacious; preferably reaction times of 2–5 hours or longer are used.

The reaction temperature is high enough to afford a reasonable rate of reaction and also high enough to give the degree of selectivity that is desired. On the other hand, the reaction temperature is not so high as to cause an undesired amount of decomposition or loss of yield by undesirable side reaction. Generally, temperatures above 220° C. are employed. More preferably, the temperature is at least 250° C. Somewhat higher temperatures can be used; it has been shown that undetectable amounts of ring brominated products are obtained when the reaction temperature is 265°±5° C. A true upper temperature limit for the reaction is not known. Very high temperatures may be utilized for short times. Thus, short temperature excursions above a preferred temperature range can be tolerated. In general, it is suggested that temperatures below 300° C. be employed but for short contact times, temperatures up to 350° C. can be used. The reaction pressure is not critical and any convenient pressure can be used. Ambient or slightly elevated pressures, say up to 100 p.s.i.g. are preferred.

The reaction temperature is above the normal boiling point for bromine. The bromine can be introduced into the reaction zone as a vapor, and if desired, in the presence of an inert carrier gas such as nitrogen. Alternatively, the bromine can be introduced as a liquid, for example using a fluid pressure exerted by a gas as the driving force to introduce the liquid bromine into the reaction zone. Whether bromine is introduced as a vapor or a liquid, it is preferably introduced below the surface of the m-phenoxytoluene.

After reaction, the product can be obtained by washing with water or diluted alkali, optionally in the presence of an organic solvent such as benzene. The wash liquid can be separated by known means, and if necessary, the product separated from the organic liquid by means such as distillation. In many instances, the brominated reaction mixture formed by the process of this invention can be directly used without further processing steps for making derivatives of benzylic and benzalic halides. In other words, the reaction mixture can be used directly for further synthesis without prior work-up, or product isolation or separation.

The following examples illustrate the process of this invention, but do not limit it.

EXAMPLE I

A one-pound bottle, fitted with a mechanical stirrer, thermometer, gas inlet adapter (drawn tip), and gas outlet to a caustic trap, was charged with 184.0 g (1 mole) of 3-phenoxytoluene and heated to 260° C. Bromine vapor (192 g, 1.2 mole) was then introduced into the 3-phenoxytoluene at 265°±5° C. over 3 hours. The resulting dark mixture was then cooled to room temperature and analyzed by gas chromatography. Yield: 239.7 g.

The results of this analysis showed that the crude mixture contains 68.6% of m-phenoxybenzyl bromide, 8.4% of m-phenoxybenzal bromide, 4.9% of unreacted 3-phenoxytoluene, 18.9% of other impurities, and no nuclear brominated product. Based on recovered 3-phenoxytoluene this represents a yield of 64.7% of monobromide and 6.1% of dibromide.

When the reaction was conducted in a similar manner using a temperature of 255°±5° C. and 0.11 mole of PCl₃ catalyst, the gas chromatographic analysis showed the reaction mixture contained 68.0% of m-phenoxybenzyl bromide, 11.3% of m-phenoxybenzal bromide, 0.3% of monobromo (aromatic substitution) by-product, <0.3% undesirable polybromo by-product. Based on recovered 3-phenoxytoluene this corresponds to a yield of 70.2% (180.6 g) of the benzyl bromide and a yield of 9.0% (30.0 g) of the benzal bromide. With PCl₃ the GC closure was 83.8% and without PCl₃ 81.9%.

EXAMPLE II

3-Phenoxytoluene (184 g, 1 mole) in a 500-ml flask, which was equipped with a mechanical stirrer, a thermometer, a gas inlet tube extended to the bottom of the flask, and a condenser vented into ice water was heated to 265° C. with stirring. Bromine vapor carried by nitrogen was passed into the hot (265°–268° C.) stirred 3-phenoxytoluene over 3 hours. The bromine vapor was generated by submersing a 100-ml flask which contained 192 g (1.2 mole) bromine in a warm (70°–80° C.) oil bath. A slow stream of nitrogen was swept through the bromine and bromine vapor was carried into the reaction. The reaction stopped as soon as the bromine feed was complete. The crude mixture had a weight of 233.5 g. GC analysis of the crude shows:

3-phenoxybenzyl bromide: 62.3 wt.%
3-phenoxybenzal bromide: 3.2 wt.%
Unreacted 3-phenoxytoluene: 7.7 wt.%

No ring-brominated products were detected. The conversion was 90.2% based on the 3-phenoxytoluene. The yields of 3-phenoxybenzyl bromide and 3-phenoxybenzal dibromide are 61.1% and 2.4 respectively, for a combined yield of 63.5%. The results of Example II appear in the following table as Run 4. The other three runs are similar to that of Example II except 0.11 mole of PCl₃ is used as a catalyst with the reaction conditions reported.

On the table, the products identified as Nos. 1–4 are:
compound no. 1: 3-phenoxybenzyl bromide
compound no. 2: 3-phenoxybenzal bromide
compound no. 3: by-product with one ring substituted bromine
compound no. 4: by-product(s) with unspecified dibrominated by-product

TABLE 1

| Run No. | Conditions | GC (wt. %) Product 1 | 2 | 3 | 4 | 3-PT | GC Closure | Conversion (%) | Yield (g. %)* 1 | 2 |
|---|---|---|---|---|---|---|---|---|---|---|
| 1 | 250° C., Br Vapor, 3 hr, PCl₃ | 55.4 | 15.3 | 3.9 | 3.1 | 3.1 | 81.5 | 95 | 164 (65.6) | 45 (13.9) |
| 2 | 250° C., Br Vapor, 6 hr, PCl₃ | 64.6 | 3.6 | 0.3 | — | 10.3 | 78.9 | 86.7 | 154 (67.5) | 8.6 (2.9) |
| 3 | 250° C., Br liquid, 4 hr, PCl₃ | 71.8 | 2.1 | 0.1 | — | 9.3 | 83.6 | 87.7 | 174 (75.4) | 5.1 (1.7) |
| 4 | 265° C., Br Vapor, 3 hr, | 62.3 | 3.2 | — | — | 7.7 | 73.2 | 90.2 | 145 (61.1) | 7.5 (2.4) |

*All yields are based on recovered 3-phenoxytoluene

The above results suggest that satisfactory yields of benzyl and benzal halide can be obtained utilizing the above phosphorus halide-free, added u.v. radiation-free procedures with a reaction temperature above about 220° C., and a reaction pressure of from about ambient to about 100 p.s.i.g. When the pressure is elevated above ambient, means for venting byproduct hydrogen halide are provided. From 0.7 to 2.5 moles of bromine can be used per each mole portion of 3-phenoxytoluene. Reaction times of about 3–5 hours would be used, and if desired, an excess of 3-phenoxytoluene can be utilized as a diluent. Further, the exemplified results suggest extension of the process to use of chlorine rather than bromine to prepare the analogous 3-phenoxybenzyl chloride and 3-phenoxybenzal chloride. Further, it is suggested that bromine chloride can be used rather than bromine as the brominating agent.

The efficacious results obtained, as exemplified by the above examples where phosphorus halide catalysis or u.v. promotion are absent, suggest that this process can be extended to a vapor phase embodiment, that is, use of reaction conditions wherein bromine and 3-phenoxytoluene vapor are reacted. The reaction is conducted in this embodiment by utilizing a reaction temperature of from about 270° C. to about 350° C., and a short contact time, usually less than one-half hour, for example 0.5–5 minutes. The vapor phase reaction can be conducted utilizing about 0.5 to about 2.0 moles or more halogen per mole of 3-phenoxytoluene.

EXAMPLE III

3-Phenoxytoluene (263 cc, 1.5 mole) in a two-liter glass resin kettle equipped with a stirrer, thermometer, and a gas inlet at the bottom was heated to 250° C. with stirring. Chlorine vapor (102 g) carried by nitrogen at about 50% concentration was passed into the hot (249°–252° C.) stirred 3-phenoxytoluene over two hours. A total of 305.8 g of crude product was recovered which, analyzed by VPC, gave the following:

| Component | Wt % |
|---|---|
| (1) m-phenoxytoluene (unreacted) | 29.7 |
| (2) m-phenoxybenzyl chloride | 55.1 |
| (3) m-phenoxybenzal chloride | 11.3 |
| (4) monochloro by-product (aromatic substitution) | 2.0 |
| (5) polychloro by-product (aromatic substitution) | 1.0 |

3-Phenoxybenzyl chloride and 3-phenoxybenzal dichloride were 51.5% and 9.1%, respectively, based on 3-phenoxytoluene charged for a combined yield of 60.6%.

EXAMPLE IV

A second run like Example III was made except that the reaction was carried out under $N_2$ atmosphere rather than with a 50% $N_2$ stream of $Cl_2$. After two hours at 248°–251° C., 310.8 grams of crude product was recovered and analyzed by VPC as follows:

| Component | Wt % |
|---|---|
| (1) m-phenoxytoluene (unreacted) | 25.9 |
| (2) m-phenoxybenzyl chloride | 52.8 |
| (3) m-phenoxybenzal chloride | 11.8 |
| (4) monochloro by-product | 3.3 |
| (5) polychloro by-product | 2.4 |

About 79% of the $Cl_2$ was converted during reaction. Yields of 3-phenoxybenzyl chloride and 3-phenoxybenzal dichloride were 50.1% and 9.7%, respectively, based on 3-phenoxytoluene charged for a combined yield of 59.8%.

EXAMPLES V–IX

These experiments were conducted to provide conversion data and test materials of construction for a large scale reactor. The reactor used was a two-liter glass resin kettle with various metal samples in the form of a coiled ⅛″ diameter by 36″ welding rod. These metal samples provided surface to volume ratios equivalent to a 500-gallon reactor. The two-liter reactor was equipped with a stirrer, thermometer, and gas inlet at the bottom. In each experiment 5.7 moles of 3-phenoxytoluene were charged to the kettle reactor and heated to about 260° C. with stirring. A nitrogen atmosphere was maintained, but only $Cl_2$ gas was fed to the bottom of the reactor at the rate of about 100 grams per hour. Samples were withdrawn at various points and analysis was obtained by VPC. Table 2 summarizes the results. In the table, chloride refers to the meta-phenoxybenzyl chloride and dichloride refers to the meta-phenoxybenzal chloride.

In Table 2, Run No. 5 was conducted with a metal coil of Inconel 600.

Run No. 6 was a baseline run in the glass reactor.

Run No. 7 was conducted with a metal coil of Hastelloy C.

Run No. 8 was conducted with Inconel 600.

Run No. 9 was conducted with a metal coil of nickel.

TABLE 2

| Run No. | Hours Feed Time | 3-PT | CHAIN Chloride | Dichloride | RING Monochloro | Polychloro | YIELDS (%) Chloride | Dichloride |
|---|---|---|---|---|---|---|---|---|
| 5 | 1.2 | 8.6 | 52.8 | 24.6 | 6.5 | 7.3 | 54 | 22 |
| 6 | 1.0 | 63.2 | 31.2 | 2.0 | 2.6 | 0.6 | — | — |
|  | 1.25 | 56.0 | 36.4 | 3.1 | 3.4 | 0.9 | — | — |
|  | 1.5 | 47.3 | 42.5 | 4.7 | 3.6 | 1.2 | — | — |
|  | 2.0 | 34.0 | 49.9 | 8.1 | 4.4 | 2.0 | 48 | 7 |
| 7 | 1.3 | 53.7 | 39.7 | 3.7 | 1.9 | 0.7 | — | — |
|  | 1.7 | 43.2 | 47.3 | 6.2 | 2.0 | 1.0 | — | — |
|  | 2.0 | 34.2 | 52.9 | 9.0 | 2.2 | 1.5 | 50 | 7 |
| 8 | 2.0 | 40.4 | 50.2 | 6.3 | 2.1 | 0.7 | — | — |
|  | 2.5 | 30.6 | 55.4 | 10.5 | 1.9 | 1.3 | 52 | 9 |
| 9 | 1.5 | 44.9 | 46.1 | 5.7 | 2.1 | 0.9 | — | — |
|  | 2.0 | 32.0 | 54.1 | 9.0 | 2.5 | 1.2 | 52 | 8 |

The results of Table 2 show not only that various materials of construction are satisfactory for the reaction, but that the thermal chain chlorination of 3-phenoxytoluene is effective with minimal ring chlorination and good yields.

I claim:

1. A process for preparing m-phenoxybenzyl chloride, or m-phenoxybenzal chloride, or a mixture thereof, said process comprising chlorinating m-phenoxytoluene with chlorine at a temperature of about 250°–260° C., said process being conducted in the absence of a catalyst and in the absence of added u.v. radiation, said process being characterized by formation of a low amount of nuclear chlorinated by-product.

2. A process of claim 1 wherein from 0.5–2.0 moles of chlorine are used per mole of 3-phenoxytoluene.

3. A process for preparing a product selected from the class consisting of m-phenoxybenzyl chloride, m-phenoxybenzal chloride, and mixtures thereof, said process comprising reacting about 0.7–2.5 moles of chlorine with each one mole quantity of m-phenoxytoluene at a temperature of about 250°–260° C., said process being carried out in the absence of added u.v. radiation and in the absence of phosphorous halide, said process being characterized by formation of a low amount of nuclear chlorinated by-product.

* * * * *